(12) United States Patent
Jamnia

(10) Patent No.: US 8,496,475 B2
(45) Date of Patent: Jul. 30, 2013

(54) INTEGRATED, LIGHTED ULTRASONIC INSERTS

(75) Inventor: Mohammad Ali Jamnia, Chicago, IL (US)

(73) Assignee: Hu-Friedy Mfg. Co., LLC., Chicago, IL (US)

( * ) Notice: Subject to any disclaimer, the term of this patent is extended or adjusted under 35 U.S.C. 154(b) by 520 days.

(21) Appl. No.: 12/635,726

(22) Filed: Dec. 11, 2009

(65) Prior Publication Data

US 2011/0140815 A1     Jun. 16, 2011

(51) Int. Cl.
*A61C 1/00*     (2006.01)

(52) U.S. Cl.
USPC .......................................................... 433/29

(58) Field of Classification Search
USPC ................... 433/29, 118; 606/169, 171, 177, 606/178; 310/26, 21, 30; 335/205–207; 338/32 R See application file for complete search history.

(56) References Cited

U.S. PATENT DOCUMENTS

| | | | |
|---|---|---|---|
| 3,143,697 A | 8/1964 | Springer | |
| 3,281,637 A | 10/1966 | Hultquist | |
| 3,521,050 A | 7/1970 | Shagena, Jr. | |
| D269,122 S | 5/1983 | Seeley | |
| 4,388,673 A | 6/1983 | Maglica | |
| 4,608,622 A | 8/1986 | Gonser | |
| 5,139,421 A | 8/1992 | Verderber | |
| 6,095,810 A | 8/2000 | Bianchetti | |
| 6,386,866 B1 * | 5/2002 | Hecht et al. | 433/29 |
| 6,619,957 B1 | 9/2003 | Mosch et al. | |
| 7,104,794 B2 | 9/2006 | Levy | |
| 7,150,629 B2 | 12/2006 | Feine | |
| 7,165,450 B2 | 1/2007 | Jamnia et al. | |
| 7,170,019 B2 * | 1/2007 | Wong et al. | 200/61.45 M |
| 7,371,066 B2 | 5/2008 | Tamburrino et al. | |
| 8,113,831 B2 * | 2/2012 | Plank et al. | 433/29 |
| 2002/0058931 A1 | 5/2002 | Parker et al. | |
| 2006/0029901 A1 | 2/2006 | Rose et al. | |

(Continued)

FOREIGN PATENT DOCUMENTS

| EP | 0643950 A1 | 3/1995 |
|---|---|---|
| EP | 0993579 A1 | 4/2000 |

(Continued)

*Primary Examiner* — Sunil K Singh

(74) *Attorney, Agent, or Firm* — Marshall, Gerstein & Borun LLP

(57) ABSTRACT

Embodiments of a magnetostrictive device, a dental lighting system, a method of illuminating a lighting apparatus and a lighting apparatus are disclosed. The embodiments may include a lighting apparatus with a light source, an electrical power storage device and a switch. When the switch detects a magnetic field, the switch may complete an electrical connection between the electrical power storage device and the switch, thus illuminating the light source. The magnetic field may be magnetostrictively or non-magnetostrictively generated, and maybe be produced by a receptacle, a hand-piece or the lighting apparatus itself. A user may switch the light source on and off. In a magnetostrictive device, the light may be illuminated even when a tip is not activated, and the electrical power storage device may be inductively re-charged. The lighting apparatus may be included in an insert of a magnetostrictive device, such as a magnetostrictive ultrasonic hand-held dental device.

7 Claims, 8 Drawing Sheets

U.S. PATENT DOCUMENTS

| | | |
|---|---|---|
| 2006/0044823 A1 | 3/2006 | Wong et al. |
| 2006/0057537 A1 | 3/2006 | Tamburrino et al. |
| 2006/0234185 A1 | 10/2006 | Ziemba |
| 2008/0057464 A1 | 3/2008 | Rose et al. |
| 2008/0064006 A1 | 3/2008 | Quan et al. |
| 2008/0096157 A1 | 4/2008 | Ziemba |
| 2008/0176181 A1* | 7/2008 | Putz et al. .................. 433/29 |
| 2009/0162810 A1 | 6/2009 | Werner et al. |
| 2009/0202961 A1 | 8/2009 | Fani et al. |
| 2011/0003823 A1 | 1/2011 | Horn |
| 2011/0017622 A1 | 1/2011 | Guenter et al. |
| 2011/0017623 A1 | 1/2011 | Guenter et al. |
| 2011/0039229 A1 | 2/2011 | Senia |
| 2011/0051903 A1 | 3/2011 | Armencha et al. |

FOREIGN PATENT DOCUMENTS

| | | |
|---|---|---|
| EP | 1182984 A2 | 3/2002 |
| EP | 1 415 614 A2 | 5/2004 |
| EP | 1480570 A1 | 12/2004 |
| EP | 2279709 A1 | 2/2011 |
| EP | 2289457 A1 | 3/2011 |
| JP | 4625258 | 2/2011 |
| WO | WO-9901696 A1 | 1/1999 |
| WO | WO-0207632 A1 | 1/2002 |
| WO | WO-2009085292 A1 | 7/2009 |
| WO | WO-2009117464 A1 | 9/2009 |
| WO | WO-2010/068435 A1 | 6/2010 |
| WO | WO-2010146228 A1 | 12/2010 |

* cited by examiner

INTEGRATED, LIGHTED ULTRASONIC INSERTS

BACKGROUND OF THE DISCLOSURE

1. Field of the Disclosure

This disclosure relates generally to integrating an electrical power source with a light source in an apparatus, and switching the light source on and off based on a magnetic field. Some embodiments of the disclosure relate to switching a lighted insert on and off in a magnetostrictive device such as a hand-held ultrasonic magnetostrictive dental device.

2. Background Description

Magnetostrictive ultrasonic dental hand-pieces are used in dentistry to remove calculus from teeth and perform other cleaning or abrasive operations by vibrating a metal insert at an ultrasonic frequency. A magnetostrictive ultrasonic dental hand-piece typically receives electric current having a controlled frequency from a generator and translates the received electrical energy into a mechanical motion of a tip of an insert coupled to the dental hand-piece. To this end, a magnetostrictive dental hand-piece includes an electrical connector, a coil, and a housing functioning as a handle. Alternating current provided to the coil induces a corresponding alternating magnetic field. At a resonant frequency, a stack of metal plates disposed within the coil may vibrate in response to the alternating magnetic field, and these vibrations may be transferred to the tip.

Since a mouth is a small and dimly-lit space in which to work, it is desirable to have an ultrasonic dental tool that can bring light directly into and around the working area, e.g., tooth and gumline surfaces. It is further desirable to omit an additional power cord for the light to minimize the number of obstructions that may get in the way of a dental practitioner's task at hand. Several known approaches exist where light is delivered to the tip end of a magnetostrictive insert by using available power in the coil of the hand-piece without needing an additional power cord.

In one known approach, a magnetostrictive ultrasonic dental insert includes a first coil or transducer for generating ultrasonic vibrations and producing the mechanical motion of the dental tip. A second coil or transducer generates a voltage signal in response to the mechanical movement. A light source in the vicinity of the tip receives the voltage signal from the second transducer and illuminates. This approach has several disadvantages. First, the intensity of the generated light may vary based on power fluctuations delivered to the first coil, such as when an operator varies tip vibration rate by varying the power to the hand-piece. Second, the intensity of the light may vary based on the integrity of the stack itself. Furthermore, this approach does not allow the light source to be turned on when the tip is not vibrating, as the voltage generated by the second transducer and used to illuminate the light source necessarily requires energizing the first transducer and stack.

In another known approach, a magnetostrictive ultrasonic dental device includes a similar primary coil for generating ultrasonic vibrations and the mechanical motion of the dental tip. A secondary coil is positioned to be inductively coupled to the primary coil and electrically connected to the light source. The secondary coil is oriented so that a magnetic field induced by energizing the first coil induces, in turn, a current flow in the second coil that causes the light source to illuminate. Like the first discussed approach, this other approach also suffers from varying intensities of the light source based on power fluctuations delivered to the first coil. Similarly, in this approach, the light source may not be turned on independent from tip vibration.

BRIEF SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Embodiments of a magnetostrictive device with a lighted insert are disclosed. The lighted insert may include a light source and an electrical power storage device or power pack (also referred to herein as an "electrical storage device"). The insert may also include a switch. When the switch detects the magnetic field generated by the magnetostrictive device, the switch may cause a completion of an electrical connection between the electrical storage device and the light source, thus illuminating the light source. The switch may include a sensor for detecting the magnetic field, and a transistor coupled to the sensor for completing the electrical connection.

Embodiments of a lighting system for a hand-held dental delivery device are disclosed. The lighting system may include a hand-piece with a coil and an insert with a tip, where the insert is enabled to be insertably engaged to the hand-piece. The tip may move in response to a magnetic field induced by current applied to the coil in the hand-piece. The insert may include a light source and an electrical power storage device or power pack. The insert may also include a switch, where a detection, by the switch, of the magnetic field induced by the coil may cause a completion of an electrical connection between the electrical storage device and the light source, thus illuminating the light source. The switch may include a sensor for detecting the magnetic field, and a transistor coupled to the sensor for completing the electrical connection. The lighting system may include a user-activated switch for interrupting and re-establishing the electrical connection. The lighting system may include a current adjustor that may modify the current applied to the coil (and, accordingly, modify the resultant magnetic field) so that the light source may be illuminated even if the tip is not vibrating or moving.

Embodiments of a method of illuminating a lighting apparatus are disclosed. The method may include disposing a light source, an electrical power storage device or power pack, and a switch within a lighting apparatus; coupling the lighting apparatus to a receptacle or hand-piece; detecting a magnetic field generated by a magnetic field source disposed within the receptacle or hand-piece; and upon the detection of the magnetic field, electrically connecting the light source and the electrical storage device, thereby illuminating the light source.

Embodiments of a lighting apparatus are disclosed. The lighting apparatus may include a light source, an electrical power source and a switch. When the switch detects the magnetic field, the switch may cause a completion of an electrical connection between the electrical storage device and the light source, thus illuminating the light source. The switch may be a Hall-effect sensor, or the switch may include a piezoelectric material.

The embodiments of the present disclosure provide numerous benefits. For example, in the present disclosure, the light source is powered by an electrical power storage device or power pack and not by power delivered to the device itself.

Thus, power fluctuations to the device do not affect the intensity of the light source at all. By using the electrical storage device, the light source generally may deliver a light at a steady, desired level of intensity with minimal fluctuations. Similarly, by using the electrical storage device, power fluctuations based on an integrity of a stack within a magnetostrictive device also do not affect light intensity. In some embodiments, the electrical storage device may be conveniently re-charged via induction.

Furthermore, the present disclosure allows the light source to be illuminated even when a tip of a magnetostrictive device is not moving. In fact, the present disclosure provides embodiments that allow a user to control whether the light source is on or off independently, from a user perspective, of whether or not the tip is activated.

Moreover, embodiments of the present disclosure allow the light source to be illuminated not via magnetostriction but via a permanent magnet or other magnetic element. With these and other embodiments, light may be conveniently and easily provided at sites where the presence of electrical cords may be cumbersome, inconvenient or even impossible.

DETAILED DESCRIPTION OF THE PREFERRED EMBODIMENTS

Although the following text sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments could be implemented, using either current technology or technology developed after the filing date of the application for this patent, which would still fall within the scope of the claims.

Figure 1:
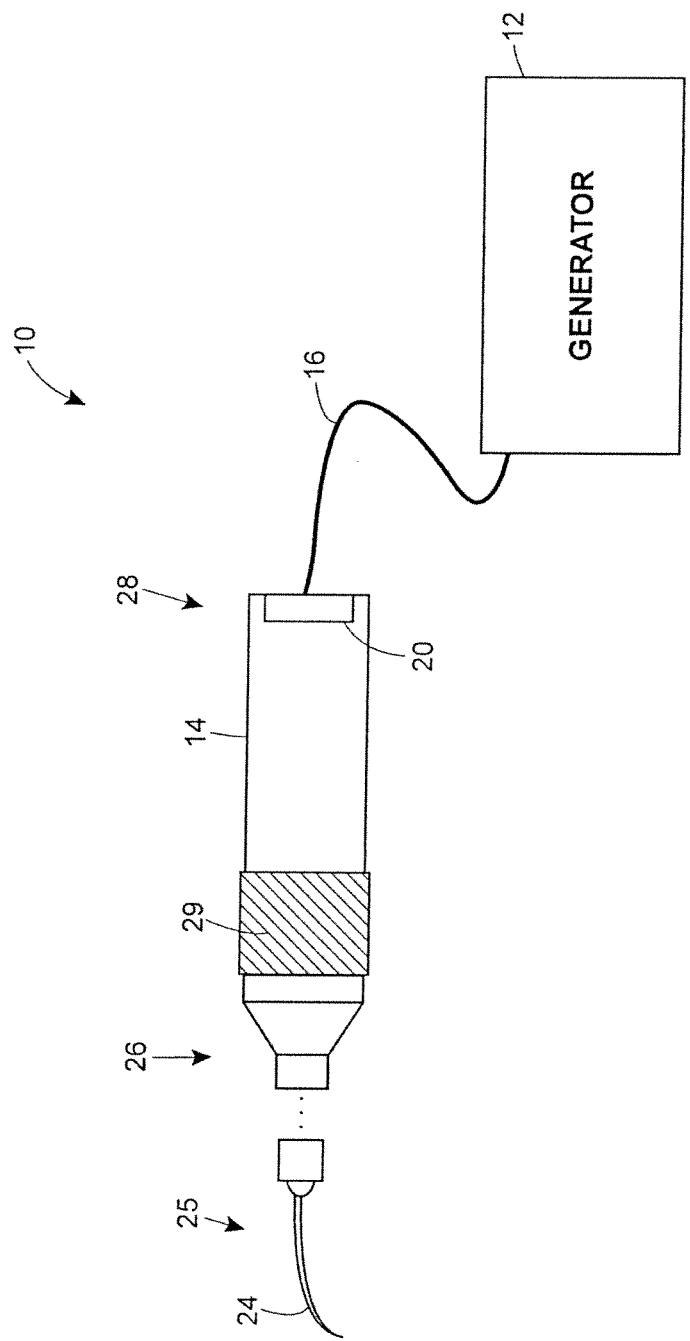
FIG. 1 schematically illustrates an ultrasonic dental system, including a signal generator, a hand-piece, and a dental insert, in which an insert consistent with the present disclosure may operate.

FIG. 1 illustrates an exemplary ultrasonic dental system 10. A dental practitioner may use the dental system 10 to remove calculi from a patient's teeth or to perform scaling, abrasion, or other similar dental procedures. In particular, a generator 12 may generate pulse width modulated (PWM) or alternating electric current (AC) at a controlled, typically ultrasonic frequency such as 25 or 30 KHz. The generator 12 may then supply the current to a hand-piece 14 via a cord 16. The hand-piece 14 may be provided with a port 20 including one or more electrical connectors and, optionally, a fluid connector to receive a supply of liquid, air, or both.

The hand-piece 14 may translate the electrical energy received from the generator 12 into mechanical energy by inducing an electro-magnetic field and applying this field to a vibrating or otherwise movable component. In particular, the hand-piece 14 may vibrate a tip 24 of an insert 25 at a frequency dependent on the driving AC frequency supplied by the generator 12, the physical dimensions of the tip 24, and the internal circuitry of the hand-piece 14. Although illustrated in FIG. 1 as an integral component, the insert 25 may include several parts, some of which may be further detachable, to facilitate, for example, cleaning, maintenance and recharging. One of ordinary skill in the art will also appreciate that the transducer for converting the energy supplied by the generator 12 into a vibratory motion of the tip 24 may be disposed in the hand-piece 14, in the insert 25, or in a separate component interacting with the hand-piece 14 and the insert 25.

The hand-piece 14 may have a tubular, rectangular, or other elongated form. The insert 25 may engage the hand-piece 14 at a patient-proximal end 26. Accordingly, the port 20 may be disposed at the patient-distal end 28. The operator may hold the hand-piece 14 at or about the grip section 29. Although the grip section 29 may be integral with the body of the hand-piece 14, FIG. 1 schematically illustrates a removable grip made of a different material than the external layer of the hand-piece 14. At least the middle section of the hand-piece 14 may be ergonomically shaped to provide an easy grip for the operator.

Figure 2:
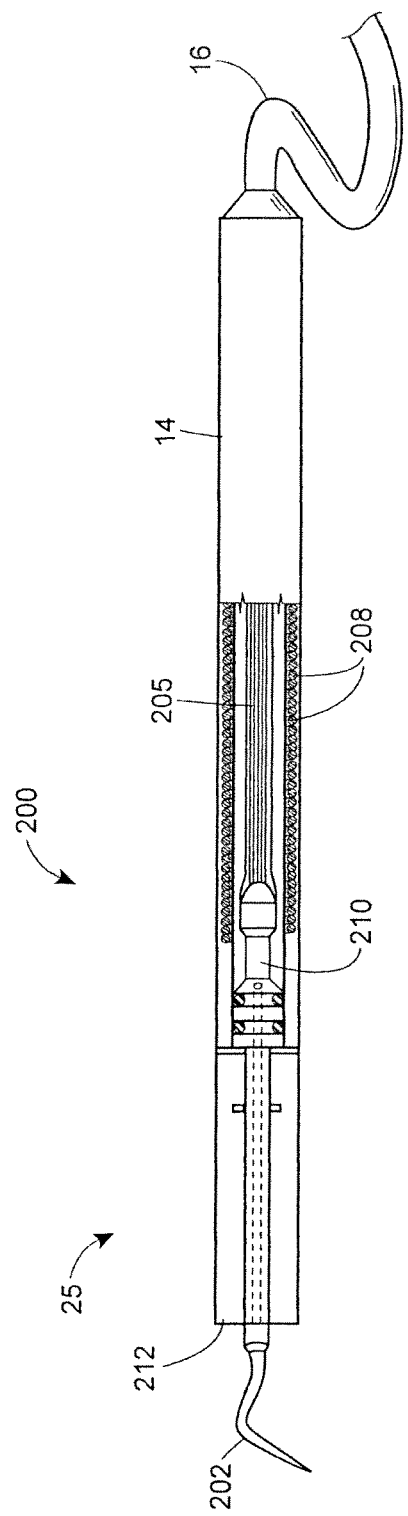
FIG. 2 is a cutaway view of the dental system of FIG. 1 with the insert engaged within the hand-piece.

FIG. 2 is a cutaway view 200 of the exemplary dental system 10 with the insert 25 insertably engaged with the hand-piece 14. The hand-piece 14 may be connected with the cord 16 that may provide the electrical connection to the generator to drive a tip 202 of the magnetostrictive insert 25.

The insert 25 may include a magnetostrictive stack 205 typically formed of nickel or nickel alloy plates that may be soldered together at each end. When the insert 25 is insertably engaged with the hand-piece 14, the stack may be encircled by or may be in proximity to a coil 208 in the hand-piece 14. The coil 208 may receive electrical energy via the cord 16, and may induce a magnetic field. The stack 205 may respond to the induced magnetic field. For example, at a corresponding resonant frequency, the stack 205 may vibrate in response to the magnetic field. Although FIG. 2 illustrates a magnetostrictive stack 205 of thin metal plates, in other embodiments, any type, shape and/or configuration of a magnetic element (e.g., the stack, a rod, a pin, etc.) responsive to a magnetic field may be used. The magnetic element may be formed, at least partially, from any suitably magnetic, ferromagnetic, diamagnetic, and/or paramagnetic material that exhibits or can be made to exhibit attraction and/or repulsion to a magnetic or electromagnetic field.

The stack 205, rod or other magnetic element may be connected to an ultrasonic horn or a velocity transducer 210 which may, in turn, be connected to the tip 202 covered with a grip 212. In this illustration, the tip 202 is illustrated as a scaling tip, but any known tip for a dental procedure may be used in conjunction with embodiments of the present invention. The velocity transducer 210 may be integral with the tip 202 or may be threaded to provided threaded connection with the tip 202. Thus, a vibration of the stack 205 in response to an induced magnetic field at a resonant frequency may cause (via the velocity transducer 210) the tip 202 to vibrate accordingly. As known in the art, the resonant frequency may not be an exact, precise frequency. Real-world factors such as impedance and a physical condition of the stack or magnetic element may come into play, so that a resonant frequency may include a narrow range of frequencies around an exact frequency that may still effect the vibration of the stack 205.

Figure 3:
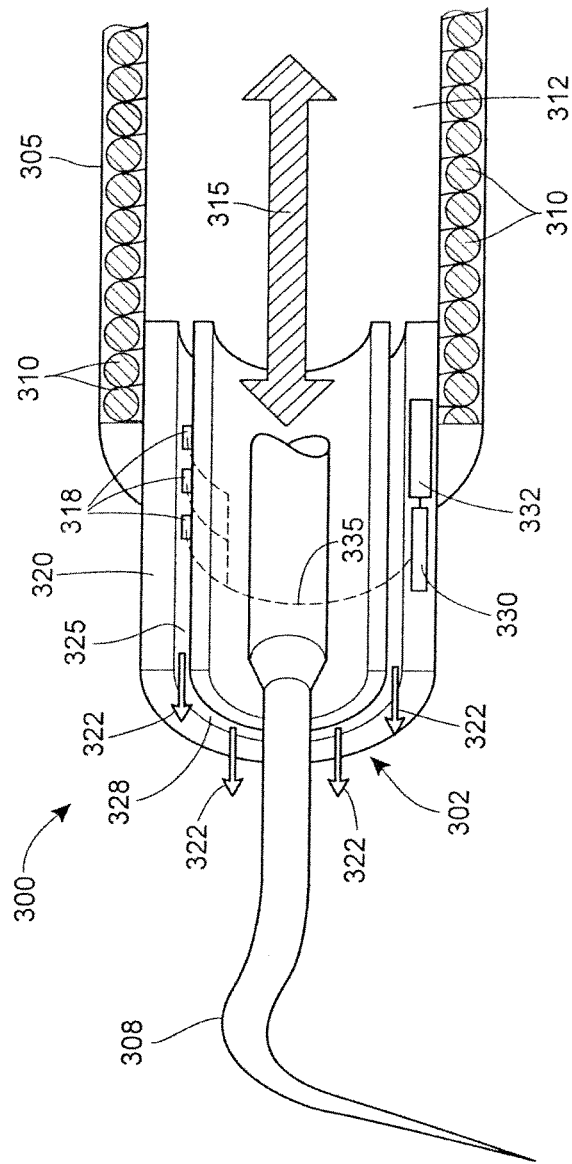
FIG. 3 is an embodiment of a lighted insert of the present disclosure engaged in a magnetostrictive hand-held dental device.

FIG. 3 illustrates an embodiment 300 of a lighted insert 302 in a magnetostrictive handheld dental device. Generally, the lighted insert 302 may take advantage of the magnetic field produced by the magnetostrictive device to switch a light source on and off. The lighted insert 302 may be used in conjunction with the dental system 10 of FIGS. 1 and 2.

In FIG. 3, the lighted insert 302 is depicted as insertably coupled to a dental device hand-piece 305. The lighted insert may include a tip 308 coupled to a magnetic element (not shown) such as the stack 205 of FIG. 2 or some other magnetic element. The hand-piece 305 may include a coil 310 to which electrical current may be applied. The coil 310 may encircle a female port 312 of the hand-piece 305 into which the insert 302 may extend when the insert 302 is engaged with the hand-piece 305. An alternating magnetic field 315 may be induced by alternating current flowing through the coil 310, and the tip 308 may move in response to the alternating magnetic field 315 (for example, in a manner as previously discussed with respect to FIG. 2).

A light source 318 may be disposed within the insert 302. In the embodiment 300, the light source 318 is shown as a set of one or more Light Emitting Diodes (LEDs) disposed within a housing 320 of the insert 302. Light 322 produced by the LEDs 318 may be channeled via a light pipe 325 to an annular port 328 near the tip 308 of the insert 302, thus providing illumination to a work area.

While the light source 318 is depicted as a set of LEDs 318 disposed within the housing 320 of the insert 302, this embodiment is only exemplary. In fact, the light source 318 may any known type of light generating source, such as one or more incandescent bulbs, neon bulbs, light rings, and the like. Moreover, the light source 318 need not be disposed within the housing 320 of the insert 302. For example, a light ring may be annularly centered around a longitudinal axis of the insert anywhere along the length of the insert 302. Furthermore, the port 328 is not required to be annular, but may be take any shape. In other embodiments, the port 328 may not encircle the tip 308 but may be disposed on one side of the tip 308.

In another example, a light source 318 may be directly disposed near the tip 308 of the insert 302 so that light may be directly delivered to the work area without requiring any light pipe 325 or channel. Indeed, the light source 318 may take any known form and be located anywhere on or in the insert 302 so long as an electrical connection 335 to an electrical storage device 330 is possible.

The housing 320 of the insert may also include an electrical power storage device or power pack 330 that provides power to the light source 318. Generally, the electrical power storage device may be self-contained and may be entirely disposed within the housing 320. The housing 320 may also include a switch 332. The switch 332 may turn the light source 318 on and off by making and breaking an electrical connection 335 between the light source 318 and the electrical power storage device 330. In particular, when the switch 332 detects the magnetic field 315, the switch may make the electrical connection 335, and when the switch 332 no longer detects the magnetic field 315, the switch may break the electrical connection 335. Thus, the switch 332 may be disposed at a location in the insert 302 so that, when the insert 302 is attached to the hand-piece 305, a presence or absence of the magnetic field 315 may be detectable by the switch 332.

A user-activated switch (not shown) may be provided so that a dental practitioner or user may control whether or not the light 318 is on or off while the tip 308 is vibrating. For example, when the user desires the light 318 to turn off, he or she may indicate "off" via the user-activated switch. The user-activated switch may interrupt the electrical connection 335 between the electrical storage device 330 and the light source 318. Similarly, when the user desires the light 318 to turn on, he or she may indicate "on" via the user-activated switch, and the user-activated switch may re-establish the electrical connection 335. In another embodiment, an "off" indication at the user-activated switch may result in a shielding of the magnetic field 315 generated by the magnetic element so that the switch 332 is unable to detect the field. In yet another embodiment, an "off" indication at the user-activated switch may result in the switch 332 being physically displaced so that the switch 332 is unable to detect the magnetic field 315. The user-activated switch may be physically located on the exterior of the hand-piece 305 or insert 302, or the user-activated switch may be remotely located, for example, on a separate hand- or foot-operated control in communicative connection with the insert 302 and/or the hand-piece 305. In any event, the user-activated switch may preferably be sealed or otherwise configured to prevent water, saliva, debris or other undesired artifacts from entering the hand-piece 305 and/or the insert 302. Other embodiments of a user-activated switch may alternatively or additionally be possible.

Figure 4:
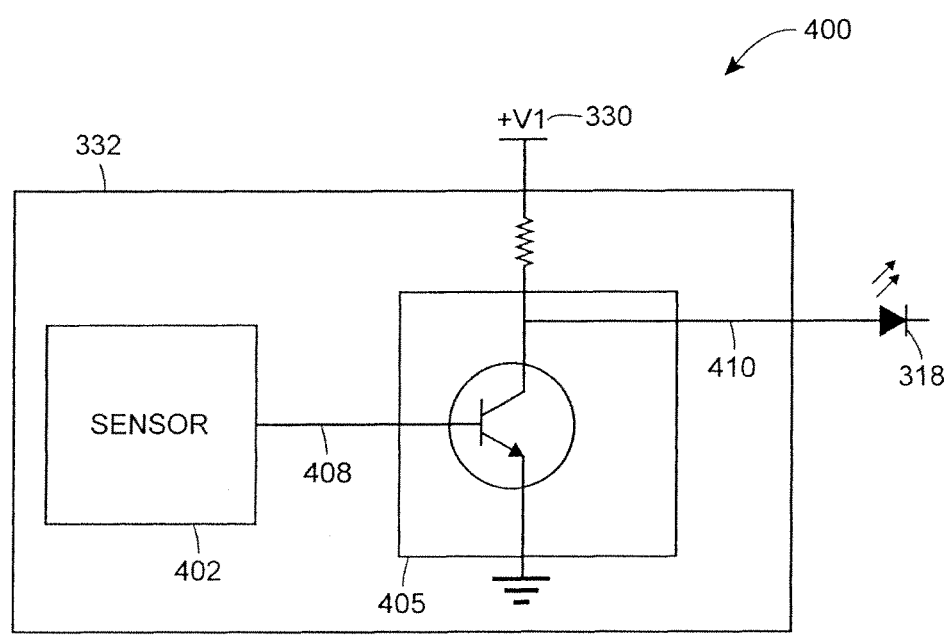
FIG. 4 is an exemplary circuit diagram of the switch from FIG. 3.

FIG. 4 depicts a circuit diagram 400 including details of the switch 332 of FIG. 3. The electrical power storage device 330 and the light source 318 are represented in FIG. 4 by their respective schematic symbols. The switch 332 may include a sensor 402 electrically coupled to a transistor 405. As in FIG. 3, the light source 318 is depicted as an LED, but other types of light sources may be used. The sensor 402 may be any sensor that generates a voltage upon detecting a magnetic field. The transistor 405 is depicted as a Bipolar Junction Transistor (BJT), however, the switch 332 is not limited to using only a BJT but may include any known transistor such as a Field Effect Transistor (FET), an Insulated Gate Bipolar Transistor (IGBT), or other suitable type of transistor.

When the sensor 402 detects a magnetic field, the sensor 402 may generate a voltage which may be delivered to the base 408 of the transistor 405. The generated voltage may be at a level sufficient to activate the transistor 405. Upon activation of the transistor 405, the output 410 of the transistor may be "on" or "high," thus completing an electrical connection between the electrical storage device 330 and the light source 318. The completed electrical connection between the electrical storage device 330 and the light source 318 may cause the light source 318 to illuminate. Similarly, when the sensor 402 no longer detects the magnetic field, the voltage generated by the sensor 402 may drop, the transistor 405 may deactivate, the electrical connection between the electrical storage device 330 and the light source 318 may be discontinued, and the light source 318 may cease to illuminate.

In some embodiments, the sensor 402 may be a Hall-effect sensor or transducer that varies its output voltage in response to changes in a detected magnetic field. Any suitably sized Hall-effect sensor known in the art may be used in conjunction with embodiments of the present disclosure.

In some embodiments, the sensor 402 may include piezoelectric material. One such example may be a bi-material, piezoelectric-based sensor including a strip of two overlapping layers or leaves. One layer may include magnetostrictive material, and the other layer may include piezoelectric material. A length of the magnetostrictive material may change in the presence of the magnetic field, and due to the differences in the lengths of the two layers, the strip may bend. The bending of the strip may induce a change of length in the piezoelectric material that may lead to a production of an electric charge. In this manner, the bi-material piezoelectric-based sensor may deliver an output voltage to the transistor 405.

Another example of a sensor including piezoelectric material may be a piezoelectric-based sensor that has a shape similar to dumbbell, where two larger-diameter ends are interconnected via a smaller-diameter section. One of the ends of the piezoelectric-based sensor may be formed from rigid, non-magnetic, non-magnetostrictive material. The other end may include a permanent magnet or other rare-earth magnetic material. The interconnecting, smaller-diameter section may be formed at least partially from piezoelectric material. In response to an alternating magnetic field, the permanent magnet end of the piezoelectric sensor may move and may cause the interconnecting, piezoelectric material to flex. An electric charge may result, and the piezoelectric-based sensor may deliver an output voltage to the transistor 405.

Of course, the sensor 402 is not limited to being only a Hall-effect type sensor or to being piezoelectric-based. Any suitable sensor 402 that generates a voltage upon detecting a magnetic field may be used in conjunction with the present disclosure.

Turning back to FIG. 3, the electrical power storage device or power pack 330 may be of a size sufficient to illuminate the light source 318 when connected to the light source 318. As used herein, the terms "electrical power storage device," "electric storage device," and "power pack" are used interchangeably to mean a power density device or a device that stores electrical energy. Generally, the electrical storage device may be self-contained and may not rely on any other electrical power source. For example, the electrical storage device 330 may be a single battery or may be a battery pack. The electrical storage device 330 may be any suitable type of known disposable, replaceable or rechargeable battery. In some embodiments, the electrical power storage device or power pack 330 may be another type of power density device, such as a supercapacitor, an electrochemical double layer capacitor (EDLC), or an ultracapacitor.

For embodiments where the electrical storage device 330 is a rechargeable battery, the battery may be recharged, for example, by removing the battery from the insert 302, placing the battery into a separate charging device, and returning the battery to the insert 302 after it has been charged. In another example, the electrical storage device or power pack 330 may be a battery pack with a charging connection port, and the battery pack may be recharged by plugging a charging cord directly into the charging connection port.

Figure 5:
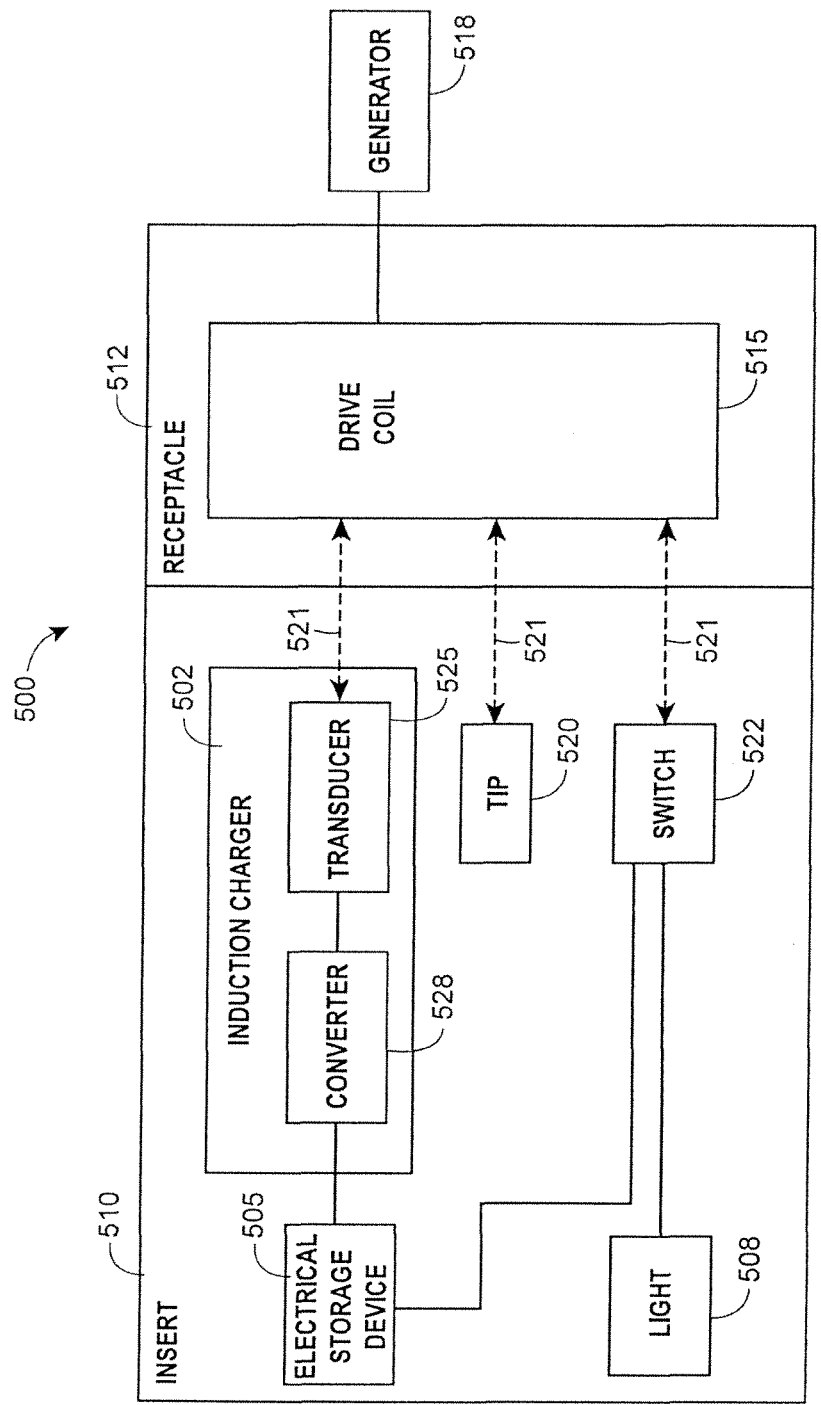
FIG. 5 is an embodiment, in block diagram form, of a magnetostrictive ultrasonic device with an induction charger.

In yet another example, the electrical storage device 330 may be partially or entirely recharged via induction. FIG. 5 illustrates an embodiment, in a block diagram form, of a magnetostrictive ultrasonic device 500 that includes an induction charger 502 for a rechargeable electrical power storage device or power pack 505 that powers a light source 508 of an insert 510. The induction charger 502 may operate in conjunction with embodiments of the dental system 10 of FIGS. 1 and 2, with embodiments of the magnetostrictive dental device 300 of FIG. 3, and/or with embodiments of the switch 332 illustrated in FIG. 4.

Similar to FIGS. 1, 2 and 3, the magnetostrictive ultrasonic dental device 500 may have an insert 510 coupled to a hand-piece or other type of receptacle 512. The hand-piece or receptacle 512 may include a drive coil circuit 515 that receives alternating current from a generator or source 518 and induces an alternating magnetic field. The insert 510 may include a tip 520 that may vibrate or move in response to the alternating magnetic field 521. The insert 510 may also include a rechargeable electrical storage device 505, a light source 508, and a switch 522 for making and breaking an electrical connection between the rechargeable electrical storage device 505 and the light source 508. The switch 522 may operate in response to the alternating magnetic field 521.

The magnetostrictive ultrasonic dental device 500 may also include an induction charger 502 for recharging all or part of the electrical storage device 505. The induction charger 502 may include a transducer 525 that is positioned to be inductively coupled to the drive coil 515. The transducer 525 may, for example, produce a current induced by a magnetic field of the drive coil 515. In some embodiments, the transducer 525 may be an induction coil, but other types of suitable transducers 525 may be used in conjunction with the present disclosure. The induced current may be converted or modified 528 into a current format that may flow to the rechargeable electrical storage device 505 and may effect a re-charging of the electrical storage device 505. For example, the current from the transducer 525 may be inverted, rectified, or otherwise converted in a manner known in the art. Thus, generally speaking, the magnetic field induced by the drive coil 515 that causes the tip 520 of the insert 510 to vibrate may also be used not only to turn the light source 508 on and off, but also to recharge the electrical storage device 505 that supplies power to the light source 508 of the insert 510.

In some embodiments, the electrical storage device 505 of the insert 510 may be re-charged by physically coupling the insert 510 not to the hand-piece or receptacle 512 but to a re-charging or docking station (not shown). The re-charging station may be a separate physical entity from both the insert 510 and the receptacle 512. The re-charging station may include a magnetic field source such as a coil to which electric current is applied, a permanent magnet or other magnetic field source. The insert 510 may be physically decoupled from the hand-piece 512 and may be individually coupled to the re-charging station, or the insert 510 may remain in the hand-piece 512 and the entire magnetostrictive device 500 may be coupled to the re-charging station. When the insert 510 or the device 500 is physically coupled to the re-charging station, the transducer 525 of the induction charger 502 may produce a current in response to the magnetic field provided by the re-charging station, and the current may effect a total or partial re-charging of the electrical storage device 505.

While FIG. 5 illustrates the induction charger 502 as included in the insert 510, in other embodiments, the induction charger 502 may be omitted from the insert 510 but included in the hand-piece or receptacle 512. Alternatively, the induction charger 502 may be a separate physical entity altogether from both the insert 510 and the hand-piece or receptacle 512. For example, the induction charger 502 may reside in the re-charging station along with the magnetic field source. In this example, when the electrical storage device of an insert 510 needs re-charging, the insert 510 may be physically coupled to the re-charging station so that an electrical connection between the electrical storage device 505 and the induction charger 502 within the re-charging station may be established.

Variations on initiating the inductive recharging of the electrical storage device 505 may be possible. For example, in some embodiments, recharging may only occur when an electrical storage device 505 has drained down to a certain level. In some embodiments, recharging may initiate in response to a user indication. Other variations of inductively recharging the electrical storage device 505 may be contemplated and operate in conjunction with the contents of the present disclosure.

The description thus far has generally addressed taking advantage of an inherent magnetic field produced by a magnetostrictive device, and using the magnetic field to turn the light source on and off. In certain scenarios, however, a dental practitioner may desire to illuminate the light source without vibrating or activating the tip, for instance, when he or she merely wants to look inside a patient's mouth for inspection, without actively scaling, and without being distracted by vibration of the tip.

Embodiments of the lighted insert of the present disclosure may address these and other situations where light is desired without tip vibration. For example, the sensor in the switch of the insert may be capable of sensing both a high-level and a low-level magnetic field. The high-level magnetic field may be induced and sensed during a standard activation of the ultrasonic hand-piece with tip vibration, for example, as previously discussed with respect to FIG. 3. The low-level magnetic field may be induced at a level that is not high enough to excite the stack or magnetic element within the hand-piece, but is still detectable by the sensor. Thus, the light may be turned on by the switch even when the ultrasonic hand-piece is not activated to vibrate the tip.

Figure 6:
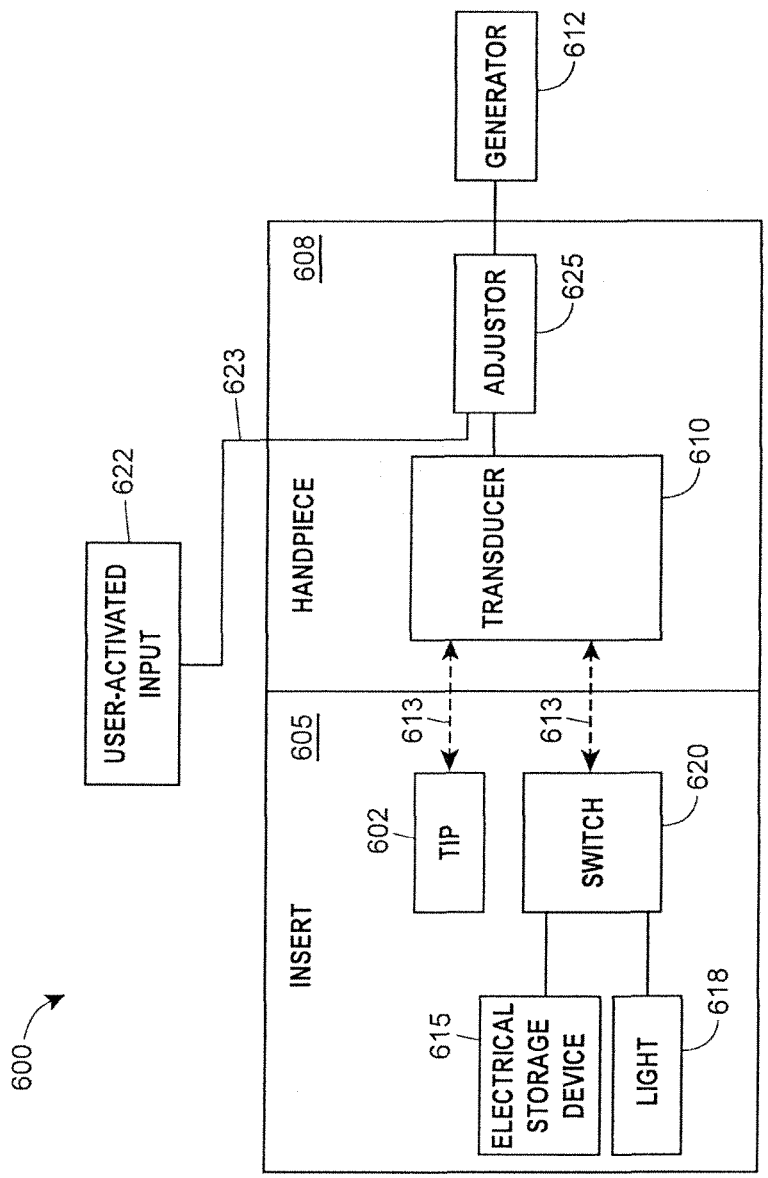
FIG. 6 is an exemplary block diagram of a magnetostrictive device with an integral light source that may be turned on and off independent of magnetostrictive activation of a tip.

To illustrate this example, FIG. 6 schematically depicts an embodiment of a magnetostrictive device 600 enabled to illuminate an integral light source even when an inserted tip 602 is not vibrating. The magnetostrictive device 600 may operate in conjunction with the embodiments of the disclosure depicted in FIGS. 1-5. The magnetostrictive device 600 may include an insert 605 (including the tip 602) that is coupled to a hand-piece 608. The hand-piece 608 may include a transducer 610 or coil that may receive electrical energy from a generator or power source 612. The tip 602 may move in response to a magnetic field 613 induced by current applied to the coil 610. The insert 605 may also include an electrical power storage device or power pack 615 and a light source 618, each of which may be coupled to a switch 620. When the switch 620 detects the magnetic field 613 induced by the coil 610, the switch 620 may establish an electrical connection between the electrical storage device 615 and the light source 618, thus illuminating the light source 618.

The magnetostrictive device 600 may also include a user-activated input 622 that may allow a dental practitioner or user of the magnetostrictive device 600 to turn on and off the light source 618 independent (from a user perspective) of an activation of the tip 602. The user-activated input 622 may be any known user interface, such as a physical switch, a touch screen, a voice command, a computer program, or the like. The user-activated input 622 may be physically coupled (not shown) to the insert 605, to the hand-piece 608, to both the insert 605 and the hand-piece 608, or the user-activated input 622 may be stand-alone and independent of the magnetostrictive device 600 altogether.

The user-activated input 622 may be communicatively coupled 623 to a current adjustor 625 in the hand-piece 608 that modifies the current delivered from the generator 612 to the transducer 610. For example, if the user indicates, via the user-activated input 622, that he or she desires the light source 618 to be on without the tip vibrating, the adjustor 625 may modify the current from the generator 612 so that the transducer 610 produces a magnetic field that is detectable by the switch 620 but does not cause the tip 602 to vibrate. In some embodiments, the adjustor 625 may be a current limiter that may modify an amplitude of the current so that the magnetic field is detectable by the switch 620 but is not sufficient to excite a stack of plates or other magnetic element (not shown) coupled to the tip 602. In other embodiments, the adjustor 625 may be a frequency converter that may modify a frequency of the applied current so that a frequency of the magnetic field is less than or more than a resonant frequency of the stack. In some embodiments, both a current limiter and a frequency converter may be used to modify the applied current. Of course, other ways of adjusting the current 625 delivered to the transducer 610 may be possible. Thus, by using the current adjustor 625, the present disclosure may provide localized, directed light when the dental practitioner desires, with or without concurrent tip vibration.

Accordingly, the magnetostrictive device 600 may be enabled to operate in at least one of several modes. In a first mode of operation, both the tip 602 may vibrate and the light 618 may be illuminated. For example, in the first mode, the alternating magnetic field 613 induced by the transducer 610 may cause the stack and, consequently, the tip 602 to vibrate responsively. Simultaneously, the alternating magnetic field 613 may also cause the sensor in the switch 620 to complete the connection between the electrical storage device 615 and the light 618. In a second mode of operation, the tip 602 may not vibrate but the light 618 may be illuminated, for example, when the alternating magnetic field 613 is insufficient to cause the vibration of the stack and the tip 602 but is still detectable by the sensor in the switch 620 to effect the completion of the electrical connection between the electrical storage device 615 and the light 618. In a third mode of operation, the tip 602 may vibrate without illumination of the light 618, such as when the alternating magnetic field 613 induces the stack and tip 602 vibration but is shielded from being detected by the sensor in the switch 620. Alternatively, in the third mode, the alternating magnetic field 613 may induce the stack and tip 602 vibration and may be detectable by the switch 620, but the electrical connection between the electrical storage device 615 and the light 618 may be disrupted.

The lighted insert or apparatus of the present disclosure is not limited to being used only with magnetostrictive ultrasonic dental devices. In fact, the lighted insert or apparatus may be used with any type of magnetostrictive device, in dental or other applications, and may leverage the magnetic field produced by any magnetostrictive device to turn the light source on and off.

Figure 7:
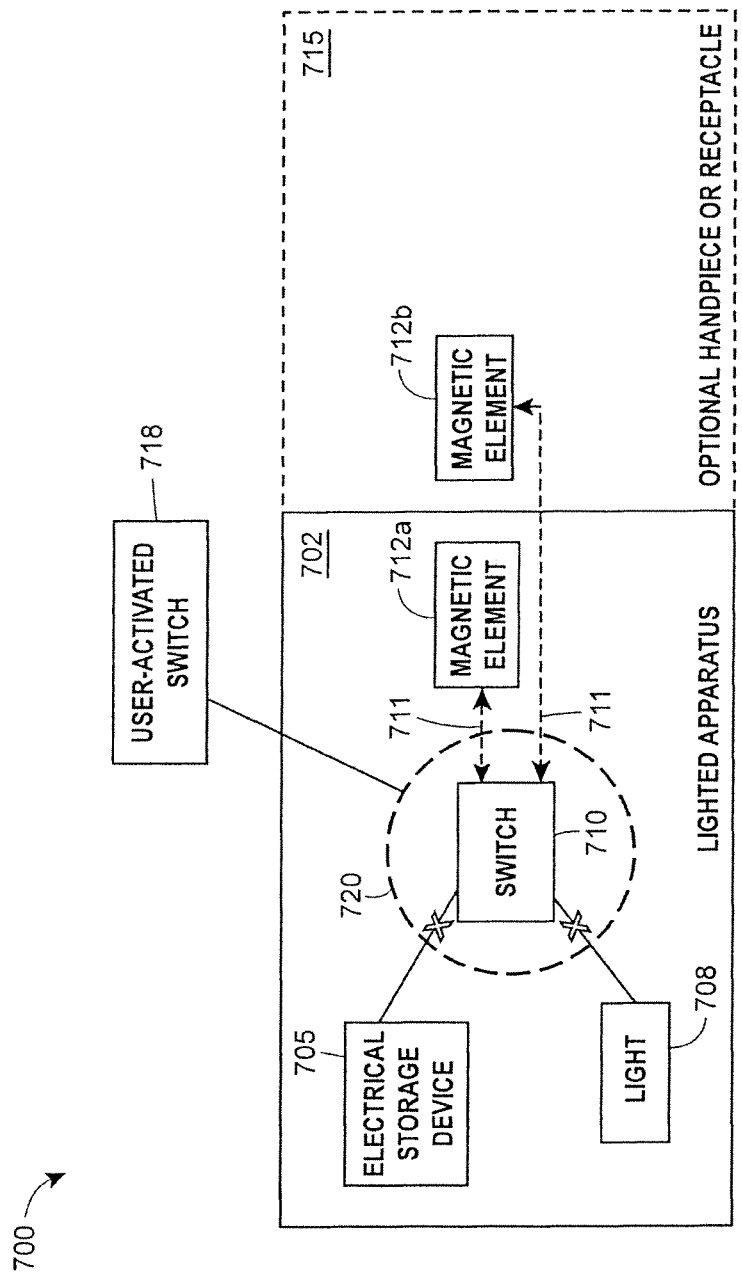
FIG. 7 depicts embodiments of a lighting apparatus responsive to a non-magnetostrictive magnetic element.

Indeed, the lighted insert or apparatus of the present disclosure is not limited to being used only with magnetostrictive devices. Any magnetic field may be leveraged to turn the light on and off. To illustrate such an example, FIG. 7 depicts an embodiment 700 in block diagram form of a lighted insert or apparatus 702 including an electrical power storage device or power pack 705, a light source 708 and a switch 710. The switch 710 may be an embodiment of the switch 332 in FIG. 4. In this embodiment 700, however, instead of the switch 710 detecting a magnetic field generated by a magnetostrictive device, the switch 710 may detect a magnetic field 711 generated by a magnetic element (as denoted by references 712a or 712b). Typically, but not necessarily, only one magnetic element 712a or 712b may be present in an embodiment, but in FIG. 7, both magnetic elements (712a and 712b) are shown as visual aids to the description. The magnetic element (712a or 712b) may be a permanent magnet, or the magnetic element 712a or 712b may be formed, at least partially, from any suitably magnetic, ferromagnetic, diamagnetic, and/or paramagnetic material that exhibits or can be made to exhibit attraction and/or repulsion to a magnetic or electromagnetic field. Upon detection of the magnetic field 711 generated by the magnetic element (712a or 712b), a sensor in the switch 710 may activate a transistor to complete an electrical connection between the electrical storage device 705 and the light source 708 and illuminate the light source 708.

In some embodiments, the lighted apparatus 702 may be inserted into a hand-piece or other type of receptacle 715 that includes the magnetic element 712b disposed therein. In some embodiments, the lighted apparatus 702 may be connectively attached to the exterior of a hand-piece of receptacle 715, such as by encircling the receptacle with the apparatus 702 or by coupling the apparatus 702 to one side of the receptacle 715. The hand-piece 715 need not be electrically powered. The magnetic element 712b in the hand-piece 715 may provide the magnetic field detected by the switch 710 in the apparatus 702 to illuminate the light source 708.

In other embodiments, a hand-piece 715 may not be used at all. The magnetic element 712a may be disposed within the lighted apparatus 702 itself, and the apparatus 702 may be used independently as a stand-alone device for illuminating the light source 708.

In these and other embodiments with a non-magnetostrictive magnetic element (712a or 712b) generating the magnetic field, the switch 710 inside the apparatus 702 may constantly be subject to the magnetic field 711 and thus the light 708 may be constantly switched "on." A user-activated switch 718 may be provided so that a user may control whether or not the light 708 is on or off. For example, when the user desires the light 708 to turn off, he or she may indicate "off" via the user-activated switch 718. The user-activated switch 718 may interrupt the electrical connection between the electrical storage device 705 and the light source, denoted in FIG. 7 by either one or both of the "X's" within circle 720. Similarly, when the user desires the light 708 to turn on, he or she may indicate "on" via the user-activated switch 718, and the user-activated switch 718 may re-establish the electrical connection. In another example (not illustrated), an "off" indication at the user-activated switch 718 may result in a physical displacement of the magnetic element (712a or 712b) or a shielding of the magnetic field 711 generated by the magnetic element (712a or 712b) so that the sensor is not able to detect the field 711. Other embodiments of using an user-activated switch 718 to turn the light source 708 on and off may alternatively or additionally be possible.

Embodiments of FIG. 7 that do not require magnetostrictive hand-pieces may expand the fields in which the disclosed lighted insert may have application. For example, the lighted insert may be used as a hand-held flashlight or a hand-held work light not only in dental applications, but in any field where light is desired such as surgical sites, automotive engines, or even personal reading lights. Other applications may be possible.

Figure 8:
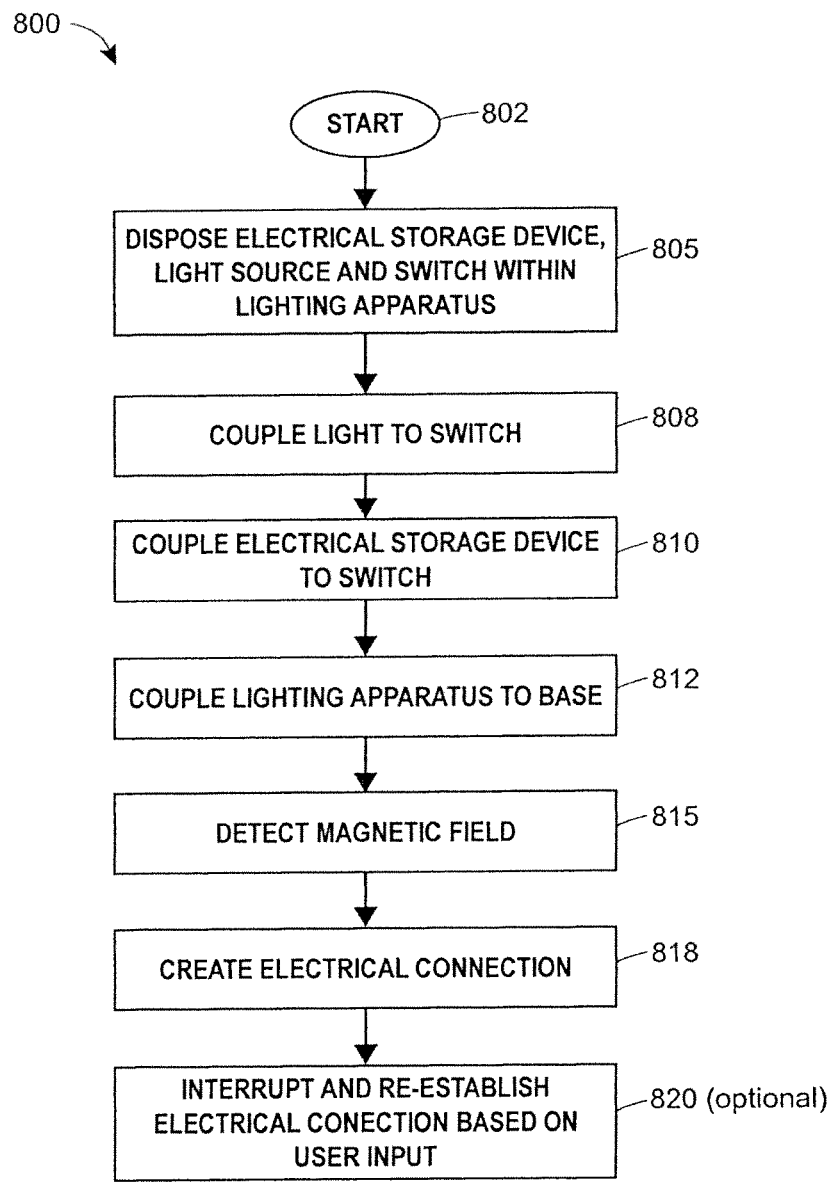
FIG. 8 depicts an embodiment of a method for illuminating a lighting apparatus.

FIG. 8 illustrates an exemplary embodiment of a method 800 for illuminating a lighting apparatus. The method 800 may be used in conjunction with any or all embodiments of the present disclosure described with respect to FIGS. 1-7.

At the start 802, the method 800 may dispose 805 a light source, an electrical power storage device or power pack, and a switch within a lighting apparatus. The light source may be any type of electrically generated light source, such as an LED, an incandescent light, a fluorescent light, a light ring, a neon light, or other type of light source. The electrical power storage device may be a single battery, a battery pack, an electric double-layer capacitor, or other known electrical storage device. The electrical power storage device may be replaceable or rechargeable. The switch may include, for example, a sensor electrically coupled to a transistor. Each of the light source, the electrical power storage device and the switch may be disposed within a housing of the insert, or may be disposed within or external to a space of the insert encircled by the housing.

At block 808, the light source may be electrically coupled to the switch. At block 810, the electrical power storage device may be electrically coupled to the switch. At block 812, the lighting apparatus may be coupled to a receptacle. In some embodiments, the lighting apparatus may be insertably coupled into the receptacle. In other embodiments, the lighting apparatus may be attached to a side of the receptacle, or may encircle the receptacle. The receptacle may be a hand-piece or a receptacle enabled to be affixed to another object or surface.

At block 815, the switch may detect a magnetic field generated by a magnetic field source disposed within the receptacle. The magnetic field source may be, for example, a coil in the receptacle to which electric current is applied. The magnetic field source may be, in another example, a magnetic element that is formed, at least partially, from any suitably magnetic, ferromagnetic, diamagnetic, and/or paramagnetic material that exhibits or can be made to exhibit attraction and/or repulsion to a magnetic or electromagnetic field. The magnetic field source may be a permanent magnet.

Upon detection of the magnetic field at the block 815, at block 818 an electrical connection may be completed between the electrical storage device and the light source, thus causing the light source to illuminate.

In some embodiments of the method 800, an optional block 820 may interrupt and re-establish the electrical connection based on a user input. The user may thus be able to control turning the light on and off.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Although the forgoing text sets forth a detailed description of numerous different embodiments, it should be understood that the scope of the patent is defined by the words of the claims set forth at the end of this patent. The detailed description is to be construed as exemplary only and does not describe every possible embodiment because describing every possible embodiment would be impractical, if not impossible. Numerous alternative embodiments could be implemented, using either current technology or technology developed after the filing date of this patent, which would still fall within the scope of the claims.

Thus, many modifications and variations may be made in the techniques and structures described and illustrated herein without departing from the spirit and scope of the present claims. Accordingly, it should be understood that the methods and apparatus described herein are illustrative only and are not limiting upon the scope of the claims.

What is claimed is:

1. A lighting system for a hand-held dental delivery device, comprising:
   a hand-piece of the hand-held dental delivery device, the hand-piece including a coil, wherein an alternating current flowing through the coil induces an alternating magnetic field;
   an insert insertably coupled to the hand-piece, the insert including:
      a tip configured for use in a dental procedure and coupled to a magnetic element, the magnetic element being one of a stack of metal plates or a rod responsive to the alternating magnetic field and disposed within the hand-piece;
      an electrical power storage device configured to generate electrical power independent of the alternating magnetic field; and
      a light source powered by the electrical power storage device and disposed so that light generated by the light source illuminates an area proximate to the tip; and
   a switch including a magnetic field sensor and a transistor, wherein:
      at a resonant frequency, the alternating magnetic field effects a movement of the magnetic element,
      the movement of the magnetic element is transferred to the tip, and
      a detection of the alternating magnetic field by the magnetic field sensor activates the transistor to form a completion of an electrical connection between the electrical power storage device and the light source, thereby causing the light source to illuminate.

2. The lighting system of claim 1, wherein the magnetic field sensor comprises at least one of a Hall-effect sensor or a piezoelectric-based device.

3. The lighting system of claim 1, further comprising a user-activated switch configured to interrupt and re-establish an electrical connection between the electrical power storage device and the light source.

4. The lighting system of claim 1, further comprising a charging device configured to be coupled to the electrical power storage device and to be inductively coupled to the coil in the hand-piece, wherein the alternating magnetic field induces the charging device to charge the electrical power storage device.

5. The lighting system of claim 4, wherein the charging device is disposed in a docking station independent of the hand-held dental delivery device and the docking station is configured to removably receive at least one of the hand-piece or the insert.

6. The lighting system of claim 4, wherein the charging device is disposed in one of the hand-piece or the insert of the hand-held dental delivery device.

7. A lighting system for a hand-held dental delivery device, comprising:
   a hand-piece of the hand-held dental delivery device, the hand-piece including a coil, wherein an alternating current flowing through the coil induces an alternating magnetic field;
   an insert insertably coupled to the hand-piece, the insert including:
      a tip configured for use in a dental procedure and coupled to a magnetic element, the magnetic element being one of a stack of metal plates or a rod responsive to the alternating magnetic field and disposed within the hand-piece;
      an electrical power storage device configured to generate electrical power independent of the alternating magnetic field; and
      a light source powered by the electrical power storage device and disposed so that light generated by the light source illuminates an area proximate to the tip; a switch including a magnetic field sensor and a transistor, wherein: at a resonant frequency, the alternating magnetic field effects a movement of the magnetic element, the movement of the magnetic element is transferred to the tip, and a detection of the alternating magnetic field by the magnetic field sensor activates the transistor to form a completion of an electrical connection between the electrical power storage device and the light source thereby causing the light source to illuminate; and
   a user interface, wherein:
      a first state selected at the user interface enables both the movement of the magnetic element and the completion of the electrical connection between the electrical power storage device and the light source, and
      a second state selected at the user interface enables the completion of the electrical connection between the electrical power storage device and the light source without the movement of the magnetic element, the second state comprising a modification of the alternating magnetic field so that an amplitude of the alternating magnetic field is greater than a level detectable by the magnetic field sensor and at least one of the amplitude or a frequency of the alternating magnetic field is less than a level required to effect the movement of the magnetic element.

* * * * *